(12) United States Patent
Draper et al.

(10) Patent No.: US 10,415,371 B2
(45) Date of Patent: Sep. 17, 2019

(54) ESTIMATING WELLBORE CEMENT PROPERTIES

(71) Applicant: Baker Hughes Incorporated, Houston, TX (US)

(72) Inventors: Ian Gareth Draper, Godalming (GB); Hermanus J. Nieuwoudt, Tomball, TX (US); Mohamed Daoud, The Woodlands, TX (US)

(73) Assignee: Baker Hughes Incorporated, Houston, TX (US)

( * ) Notice: Subject to any disclaimer, the term of this patent is extended or adjusted under 35 U.S.C. 154(b) by 239 days.

(21) Appl. No.: 15/461,648

(22) Filed: Mar. 17, 2017

(65) Prior Publication Data

US 2017/0268325 A1 Sep. 21, 2017

Related U.S. Application Data

(60) Provisional application No. 62/310,107, filed on Mar. 18, 2016.

(51) Int. Cl.
| | | |
|---|---|---|
| *E21B 47/00* | (2012.01) | |
| *E21B 49/02* | (2006.01) | |
| *G01N 1/08* | (2006.01) | |
| *G01N 33/38* | (2006.01) | |

(52) U.S. Cl.
CPC .......... *E21B 47/0005* (2013.01); *E21B 49/02* (2013.01); *G01N 1/08* (2013.01); *G01N 33/383* (2013.01)

(58) Field of Classification Search
CPC ....... E21B 47/0005; E21B 49/02; G01N 1/08; G01N 33/383
See application file for complete search history.

(56) References Cited

U.S. PATENT DOCUMENTS

| | | |
|---|---|---|
| 4,281,288 A | 7/1981 | Izumi |
| 4,748,855 A | 6/1988 | Barnoff |
| 5,168,942 A | 12/1992 | Wydrinski |
| 6,125,935 A | 10/2000 | Shahin, Jr. |
| 6,941,231 B2 | 9/2005 | Zeroug et al. |
| 7,168,508 B2 | 1/2007 | Goldberg et al. |
| 7,500,388 B2 | 3/2009 | Fujisawa et al. |

(Continued)

FOREIGN PATENT DOCUMENTS

WO 2015020530 A2 12/2015

*Primary Examiner* — Michael R Wills, III
(74) *Attorney, Agent, or Firm* — Hogan Lovells US LLP

(57) ABSTRACT

A method of estimating properties of wellbore cement by penetrating the cement, and monitoring the amount of energy or power required for penetrating the cement. Penetrators include a drill bit that bores into the cement, and probes or pins that are forced into the cement. The energy or power monitored can be current and/or voltage supplied to a motor that drives the drill bit or probe. Comparing the monitored energy or power with that required to penetrate a reference cement sample of known properties can yield information about the cement being sampled. When the wellbore is lined with multiple coaxially disposed strings of casing with cement between adjacent strings and on the outer surface of the outer string; the method further includes obtaining core samples from portions of each string, each layer of cement, and formation adjacent the wellbore.

19 Claims, 3 Drawing Sheets

(56) References Cited

U.S. PATENT DOCUMENTS

| | | |
|---|---|---|
| 7,516,802 B2 | 4/2009 | Smith, Jr. |
| 7,753,117 B2 | 7/2010 | Ramakrishnan |
| 8,171,990 B2 | 5/2012 | Tchakarov et al. |
| 8,854,044 B2 | 10/2014 | Bittar et al. |
| 2012/0234600 A1 | 9/2012 | Lee et al. |
| 2013/0308753 A1 | 11/2013 | Groves et al. |
| 2013/0340505 A1 | 12/2013 | Go Boncan et al. |
| 2014/0174192 A1 | 6/2014 | Shine, Jr. et al. |
| 2015/0247396 A1 | 9/2015 | Tunc et al. |
| 2015/0346379 A1 | 12/2015 | Wyts |
| 2017/0030157 A1* | 2/2017 | Hansen ................ E21B 49/081 |

\* cited by examiner

ESTIMATING WELLBORE CEMENT PROPERTIES

CROSS-REFERENCE TO RELATED APPLICATION

This application is a continuation in part of and claims priority to and the benefit of U.S. Provisional Application Ser. No. 62/310,107, filed Mar. 18, 2016, the full disclosure of which is incorporated by reference herein in its entirety and for all purposes.

BACKGROUND OF THE INVENTION

1. Field of Invention

The present disclosure relates to estimating properties of cement that lines a wellbore by direct interaction with the cement. More specifically, the present disclosure is directed to a method of estimating cement properties by penetrating the cement, and monitoring an amount of power or energy required for the penetration. The method further includes obtaining core samples from portions of each string, each layer of cement, and formation adjacent the wellbore.

2. Description of Prior Art

Hydrocarbon producing wellbores are typically lined with casing that is bonded to the wellbore with cement. The cement is injected within the annulus formed between the outer diameter of the casing and the inner diameter of the wellbore. The cement adheres the casing within the wellbore, and also isolates adjacent zones within the formation from one another. Isolating adjacent zones can be important when one of the zones contains oil or gas and the other zone includes a non-hydrocarbon fluid such as water. The properties of the cement behind the casing are of significant importance to the integrity of the well. Should the cement surrounding the casing be defective and fail to provide isolation of the adjacent zones, water or other undesirable fluid can migrate into the hydrocarbon producing zone thus diluting or contaminating the hydrocarbons within the producing zone. Faulty cement sometimes allows hydrocarbons to navigate up the wellbore between the casing and wellbore wall and to a location having an ignition source.

Known techniques for identifying damaged cement include installing downhole sensors for detecting fluid leakage, or deploying downhole tools that interrogate the wellbore. Example downhole tools for analyzing the integrity of wellbore cement include transducers that emit acoustic waves into the casing. Attenuation of the acoustic waves can be analyzed to estimate efficacy and integrity of the cement bond. The types of transducers used for inducing and recording the acoustic waves include piezoelectric devices and electrical magnetic acoustic transducers.

SUMMARY OF THE INVENTION

Disclosed herein is an example of a method of operations in a wellbore, and that includes deploying a testing assembly in the wellbore, where the testing assembly includes a motor and a bit, and rotating the bit by energizing the motor. Operational data of the motor is monitored, and the bit is bored into the cement. A reference database is consulted that has physical information of a plurality of reference cements, and reference operational data of a reference motor when boring into each of the plurality of reference cements, and physical information of the cement is established by correlating the monitored operational data with the physical information of the reference cement. In an example, the operational data is electricity delivered to the motor, and wherein the reference operational data is electricity delivered to the reference motor. The method further optionally includes analyzing the results of acoustic testing of the cement to obtain additional information about the physical information of the cement. The method can further include refining results inferred from an acoustic interrogation of the wellbore with the physical information of the cement established by correlating the monitored operational data with the physical information of the reference cement. In an example, the bit is a coring bit, and wherein a core sample of the cement is retrieved and analyzed. A force required to break the core sample from the cement is optionally recorded. The bit can be a drill bit having a helical flute. The physical information can be a physical property of the cement, such as mechanical specific energy, unconfined compressive strength, yield strength, density, and combinations thereof. The method can further involve assessing a need to remediate the cement based on the step of establishing physical information of the cement. In an alternative, the step of monitoring operational data of the motor is conducted prior to contacting the casing with the bit, while the bit is boring in the casing and cement, and after the bit is removed from the casing and the cement. The method can also further include confirming cement presence and integrity when forming holes prior to a cement squeeze operation. In an embodiment, the method includes confirming that the cement provides a barrier to isolate subterranean zones from one another. In one alternative, the reference database is generated by using the reference motor to bore into a plurality of reference sample assemblies, that each have reference casing and the reference cement, and by monitoring the electricity delivered to the reference motor when boring into each reference sample assembly, and populating the reference database with values of the monitored electricity that correspond to the reference cement being bored.

Also included is a method of operations in a wellbore lined with casing and cement that includes boring into the cement with a testing assembly, monitoring operational data of the testing assembly when the testing assembly is boring into the cement, consulting a reference database having physical information of a reference cement and reference operational data of a reference motor when boring into the reference cement, identifying reference operational data from the reference database having a value substantially the same as the monitored operational data, and estimating physical information of the cement in the wellbore to be the same as reference physical information that corresponds to the identified reference operational data. Optionally, the testing assembly includes a motor and a bit, and wherein the bit bores into the cement. An example of operational data includes electricity delivered to the motor, and wherein the physical information includes unconfined compressive strength.

Another example is disclosed that is a method of operations in a wellbore lined with casing and cement, and that includes penetrating the cement, monitoring an amount of energy consumed to penetrate the cement, and estimating physical information about the cement based on the step of monitoring. The physical information can include mechanical specific energy, unconfined compressive strength, the Poisson ratio, Young's modulus, yield strength, density, and other mechanical properties. The method optionally includes comparing the amount of energy consumed to an amount of energy consumed when penetrating an amount of cement having known physical information. In one alternative, the method further involves penetrating a plurality of samples of cement having known physical information, and monitoring amounts of energy consumed to penetrate each sample, and creating a database that correlates the amount of energy consumed for penetrating the cement.

BRIEF DESCRIPTION OF DRAWINGS

Some of the features and benefits of the present invention having been stated, others will become apparent as the description proceeds when taken in conjunction with the accompanying drawings, in which.

Figure 1:
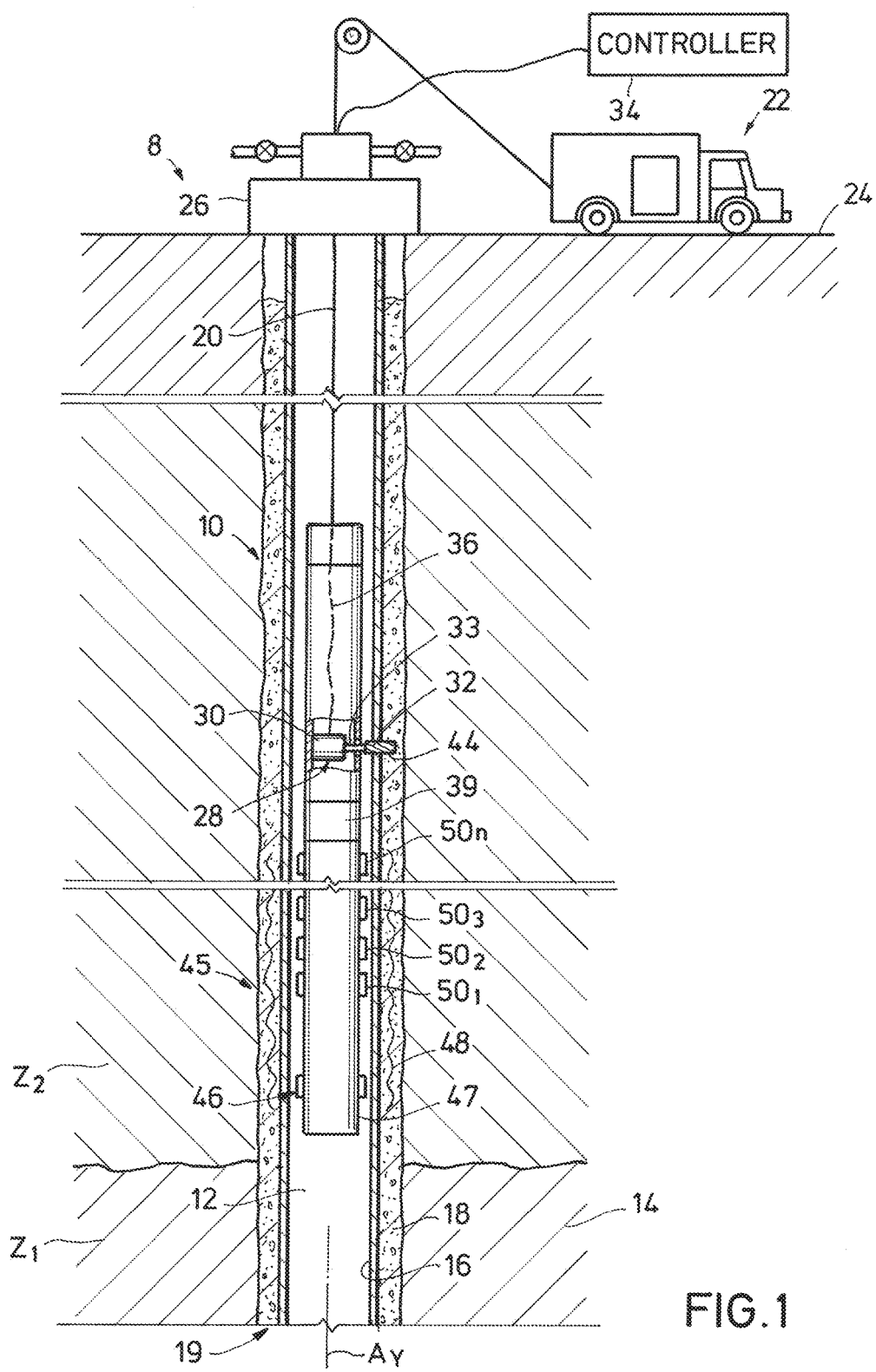
FIG. 1 is a side partial sectional view of an example of estimating properties of wellbore cement with a downhole system.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The method and system of the present disclosure will now be described more fully hereinafter with reference to the accompanying drawings in which embodiments are shown. The method and system of the present disclosure may be in many different forms and should not be construed as limited to the illustrated embodiments set forth herein; rather, these embodiments are provided so that this disclosure will be thorough and complete, and will fully convey its scope to those skilled in the art. Like numbers refer to like elements throughout. In an embodiment, usage of the term "about" includes +/−5% of the cited magnitude. In an embodiment, usage of the term "substantially" includes +/−5% of the cited magnitude.

It is to be further understood that the scope of the present disclosure is not limited to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation.

Shown in a side partial sectional view in FIG. 1 is one example of a downhole system 8 which includes a downhole tool 10 deployed in a wellbore 12. The wellbore 12 is formed into a subterranean formation 14, and casing 16 lines the wellbore 12. Cement 18 is illustrated in the annular space 19 between the casing 16 and formation 14. In the illustrated example, the cement 18 is used to bond the casing 16 to the formation 14, and to isolate adjacent zones $Z_1$, $Z_2$ in the formation 14 from communication via the annular space 19. Also included in the downhole system 8 is a wireline 20 shown attached to an upper end of the downhole tool 10 and which provides a means for deploying and retrieving the downhole tool 10 into and from the wellbore 12. Power, communication, and control signals can also be transmitted through the wireline 20 between downhole tool 10 and a surface truck 22 shown disposed on surface 24. Wireline 20 threads through a wellhead assembly 26 shown on surface 24 and over the opening of the wellbore 12.

Illustrated with downhole tool 10 is an example of a testing assembly 28 for estimating properties of the cement 18. Testing assembly 28 of FIG. 1 includes a motor 30 and a bit 32. Bit 32 is shown mounted on an end of a shaft 33 that protrudes from motor 30, and can optionally couple directly to a chuck (not shown) on motor 30. A schematic example of a controller 34 is depicted on surface 24, examples exist where controller 34 is within surface truck 22. In an embodiment, controller 34 communicates command signals to motor 30, such as for initiating operation, suspending operation, or terminating operation of the motor 30. In one alternative, data from motor 30, such as operating conditions (e.g. temperature and pressure) and operational data (e.g. electrical current delivered to or consumed by, voltage delivered to or consumed by, torque, revolutions per minute, power delivered to or consumed by, energy delivered to or consumed by, etc.) is communicated to controller 34 (or any other device on surface 24). In an example, communication between motor 30 and controller 34 is through wireline 20, or through a control line 36 shown having an end connected to motor 30. Optionally, control line 36 provides a communication link between motor 30 and wireline 20.

In one non-limiting example of operation, motor 30 is powered via electricity transmitted through wireline 20 (and optionally through control line 36). Powering motor 30 in turn causes rotation of shaft 33 or chuck, and thus correspondingly rotates bit 32. Urging the rotating bit 32 towards the casing 16, such as with an urging means (not shown) that biases the downhole tool 10 and testing assembly 28 radially within wellbore 12, puts the bit 32 into rotating contact with the casing 16. Continued urging of the bit 32 forces bit 32 through casing 16 and into the cement 18 where the bit 32 penetrates and bores into the cement 18. In an optional step, operational data of the testing assembly 28 and/or operating conditions downhole are monitored before, during, and after the bit 32 is in rotating contact with casing 16 and cement 18. As described in more detail below, comparing the monitored operational data with reference operational data can yield physical information about the cement. In a specific example, the electricity delivered to or consumed by the testing assembly 28 is monitored before, during, and after contacting the casing 16 and cement 18 with the bit 32. For the purposes of discussion herein, the term electricity includes one or more of electrical current, voltage, electrical current and voltage, electrical power, electrical energy, and combinations thereof. Examples of physical information include mechanical specific energy, unconfined compressive strength, yield strength, density, and other mechanical properties. In an example description, mechanical specific energy is the energy required to remove a unit volume of rock or other downhole formation. In an embodiment, the testing assembly 28 penetrates into the cement 18 at designated depths within the wellbore 12 by selectively raising or lowering the wireline 20.

Figure 2A:
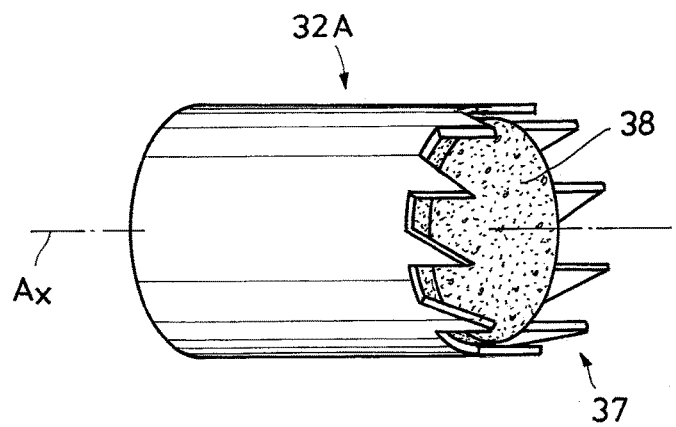
FIG. 2A is a perspective view of an example of a coring bit for use with the downhole system of FIG. 1.
Figure 2B:
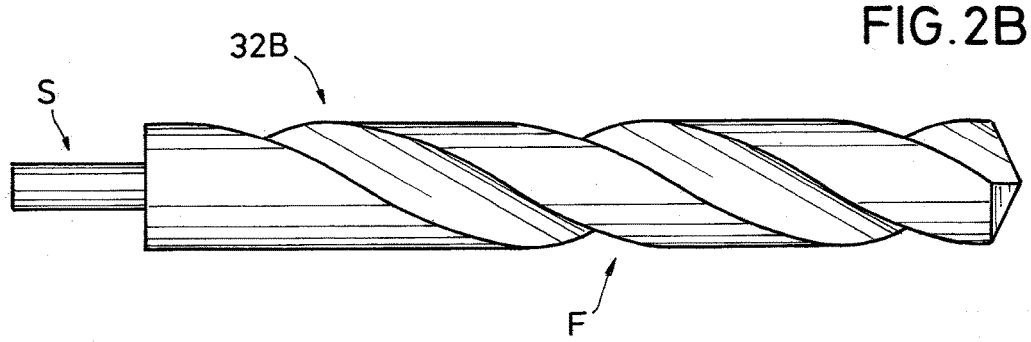
FIG. 2B is a side view of an example of a fluted bit for use with the downhole system of FIG. 1.

Referring now to FIG. 2A, shown in a perspective view is an example of the bit 32A that is tubular with a bore along its axis $A_X$, and cutting teeth 37 formed axially along one of its ends. Thus in the embodiment illustrated in FIG. 2A, bit 32A is in the form of a coring bit. Further illustrated disposed within the axial bore of bit 32A is a core sample 38 of the cement 18 which was obtained by rotating bit 32A while forcing bit 32A against cement 18. Optionally, one or more core samples 38 of the cement 18 can be obtained and stored within a housing 39 of downhole tool 10 (FIG. 1) for later analysis of the mechanical properties of the cement 18. Examples of the bit 32 can include any other type of penetrating device, such as a standard drill bit 32B shown in FIG. 2B with a shaft S and flutes F on a fluted section, where the flutes F can extend axially or helically along the fluted section. In another alternative, an elongate probe (not shown) can be employed instead of the bit 32, and which is projected radially outward from the downhole tool 10 through the casing 16, and into the cement 18. Monitoring the energy or power delivered to or consumed by motor 30 (FIG. 1), and/or force required to penetrate the cement 18 and retract the bit 32A from the cement 18 can then be correlated to physical information of the casing 16 and cement 18.

Figure 3:
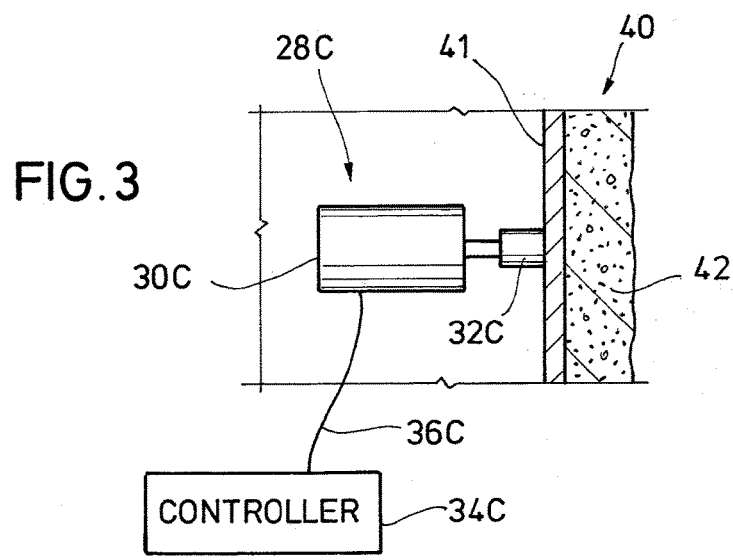
FIG. 3 is a side partial sectional view of an example of estimating properties of a reference cement with a testing system.

Shown in a side partial sectional view in FIG. 3 is an example of an embodiment of a testing assembly 28C conducting a reference boring by boring into a reference sample assembly 40. Here testing assembly 28C includes motor 30C and bit 32C, embodiments exist wherein motor 30C and bit 32C are the same, similar to, or different from motor 30 and bit 32 of FIG. 1. The reference sample assembly 40 includes a reference casing 41 and reference cement 42. In one operational example, physical information of the reference casing 41 and reference cement 42 are known or are otherwise obtainable, and during the step of the bit 32C boring into the reference casing 41 and reference cement 42, the operational data of the testing assembly 28C is monitored. Alternatively, the operational data of the testing assembly 28C is monitored while the motor 30C is energized, but prior to when the bit 32C is in contact with the reference casing 41, and also after obtaining a sample of reference cement 42 and when being withdrawn from reference casing 41. In an alternative, the operational data is monitored by a controller 34C via control line 36C.

Embodiments exist where controller 34C and control line 36C of FIG. 3 are the same as, similar to, or different from controller 34 and control line 36 of FIG. 1. Further optionally, multiple reference borings are performed where the physical properties of the reference cement 42 and/or reference casing 41 are different, and which can be done at different locations in the reference casing 41 or reference cement 42. Moreover, examples exist where reference borings are performed on multiple ones of the reference casing 41 and/or reference cement 42, and where different reference casings 41 and reference cements 42 have different properties, are made from different materials, or have different dimensions (i.e. radial thickness). At least some of the reference casings 41 and reference cements 42 have properties the same or similar to casing and cement installed downhole in a wellbore, including cement deemed as being faulty or in need of repair or replacement in order for a well to be operated in compliance with acceptable and recognized industry and governmental standards and practices.

By conducting reference borings on multiple reference sample assemblies 40 where the casing 41 and/or cement 42 of each assembly 40 has physical information that can vary, a reference database is generated containing multiple operational data records of the testing assembly 28C. In yet a further example, the reference database is expanded by further populating the database with known physical information of the reference cement 42 and/or reference casing 41 on which the reference borings were conducted. Further in the reference database, specific operational data recorded when conducting a reference boring on a particular reference sample assembly 40 are associated with the known physical information of the reference sample assembly 40 being bored. Thus the reference database contains testing assembly 28C operational data that corresponds to physical information of a particular sample assembly 28C. Explained in more detail below, is that physical information of casing and cement is obtainable by correlating operational data monitored when boring the casing and cement to physical information in the reference database. As indicated above, the operational data monitored can include one or more of the following: electrical current usage, voltage usage, torque, revolutions per minute, power delivered to or consumed by, energy delivered to or consumed by, and combinations thereof.

In one example embodiment, the testing assembly 28 bores into casing 16 or cement 18 (FIG. 1) having unknown physical information, the operating conditions and operational data of the testing assembly 28 is monitored. In a non-limiting example, correlating the monitored operational data to physical information from the reference database yields physical information about the casing 16 and/or cement 18. An example of correlating includes pinpointing a value or values of operational data from the reference database that are the same or substantially similar to the operational data monitored from the testing assembly 28 when boring the casing 16 and cement 18, and then selecting the physical information in the reference database that corresponds to the pinpointed value. The physical information selected from the reference database is deemed to reflect the actual physical information of the casing 16 and/or cement 18. In another example of correlation, monitored operational data is correlated to reference physical information either by interpolation or extrapolation of the relationships between corresponding values of the reference operational data and reference physical information.

An advantage of the method described herein over standard evaluation methods, is that the known evaluation methods typically infer the cement quality from acoustic and ultrasonic measurements, but do not contact the cement. These inferences can sometimes be ambiguous and not provide confirmation of adequate zonal isolation. The method disclosed herein on the other hand physically contacts the cement being evaluated when estimating the physical information of the cement, so that in an example the operator can confirm the cement provides a barrier that isolates subterranean zones $Z_1$, $Z_2$ from one another. Taking these measurements at discrete points helps an operator understand properties of the cement. In one optional embodiment, the measurements obtained with the method described herein can be used to refine ultrasonic measurements, and can assist one in determining a best course of action when remediating possibly defective cement or a defective cement bond. Further, use of the present method increases certainty of cement quality. Another advantage of the present method is that the hardware required for the evaluation is largely already in use, meaning existing equipment requires little to no modification. Thus in an example, implementing the present method does not require a capital cost investment to a well producer, operator, or owner. In existing cases the operators can sometimes be required to plug back and either sidetrack or abandon a well when cement quality is in doubt. The present method allows real time confirmation of cement presence and integrity when forming holes prior to a cement squeeze operation. The operator has the option of adding additional holes or increasing the spacing between holes without need to pull out of the hole; which is required in traditional squeeze operations. The method described herein can be applied in plug and abandonment operations.

Referring back to FIG. 1, in one example of operation, the motor 30 is energized from a power source (not shown), which can be in the wellbore 12, within controller 34 or surface truck 22, or on surface 24. Energizing motor 30 rotates the bit 32, and a biasing means (not shown) is initiated to urge bit 32 against the casing 16 and cement 18. As indicated above, biasing means can urge the entire tool 10 radially within wellbore 12, or can be in tool 10 and urge motor 30 or entire testing assembly 28 radially with respect to tool 10. Continued urging of the bit 32 radially from axis $A_Y$ of wellbore 12 forms a bore 44 in casing 16 and cement 18. Bore 44 optionally extends radially outward from the wellbore 12 up to, or into the formation 14. In an alternative, pressure in the bore 44 is measured to infer information about the cement 18 or formation 14. Optionally, pressure in the bore 44 is measured by the tool 10 during the coring operation. In an example, a pressure testing tool with straddle packers (not shown) is deployed in the wellbore 12 and which isolates the bore 44. In this example, fluid is injected into or withdrawn from the bore 44, and any resulting changes in pressure can be monitored adjacent the bore 44, or at different depths in the wellbore 12. Based on the monitored pressure variations caused by injection of fluid into the bore 44, or withdrawal of fluid from the bore 44, information about the cement 18 can be inferred. The information can include cement physical properties, quality of the cement, and integrity of the cement. In some instances, the bit 32 does not extend past the cement 18, and an end of the core sample 38 (FIG. 2A) distal from the motor 30 is broken away from the rest of the cement 18 prior to the bit 32 being drawn back into the tool 10. Additional information about the cement 18 can be inferred by monitoring and/or recording the amount of force or pressure exerted to break the core sample 38. In one example, the force and/or pressure for breaking a core sample 38 from a wellbore 12 is compared to the force and/or pressure for breaking a core sample from reference cement 42 (FIG. 3), and based on the comparison information about the core 38 and thus information about the cement 18 is obtained; where the obtained information includes mechanical properties of the cement 18 as well as efficacy of the cement 18. Optionally, an evaluation of the cement 18 is performed based on the obtained information, and that can be used to approve further use of the cement 18 if the information indicates a value of physical information of the cement 18 is within a designated range that is deemed acceptable. In an alternative, if the physical information has a magnitude that is outside of a designated range of acceptable values, a determination is made to repair, remediate, or replace the cement 18. Knowledge of one or more of the types of physical information listed above can be relied on to evaluate the cement 18. It is well within the capabilities of one skilled in the art to evaluate cement 18, or other material downhole (i.e. casing or formation) based on estimates of physical information obtained via the method described herein. In a further optional example, the presence or absence of micro-annuli in the cement can be identified by the method described herein.

Further illustrated in FIG. 1 is an example of an ultrasonic sensing sub 45 that is used for gathering additional information within the wellbore 12. As shown, a transmitter 46 mounts to a housing 47 of the sub 45 that when energized induces an acoustic signal 48 shown propagating through the cement. Embodiments exist wherein the signal 48 includes shear waves, compression waves, or a combination. Receivers $50_1$-$50_n$ shown spaced axially away from transmitter 46 sense the signal 48. Data representative of the signal 48 is optionally recorded within sub 45, or transmitted to the controller 34 via wireline 20. In an alternative, the recorded signal 48 is analyzed to identify physical information about the cement 18. In an alternative, results obtained by boring the casing 16 and cement 18 are combined with information gathered by the ultrasonic sensing sub 45 to increase the accuracy and precision of the physical information obtained. In an alternative, the physical information obtained about the cement 18 by the procedure described herein is used to refine acoustic information obtained by sensing sub 45, or that obtained by a previous interrogation of the wellbore 12.

In an example, controller 34 includes an information handling system ("IHS"). In addition to the control functions describe above, IHS may also be used to store recorded data as well as processing the data into a readable format. The IHS may be disposed at the surface 24, in the wellbore 12, or partially above and below the surface. The IHS may include a processor, memory accessible by the processor, nonvolatile storage area accessible by the processor, and logics for performing each of the steps above described.

Figure 4:
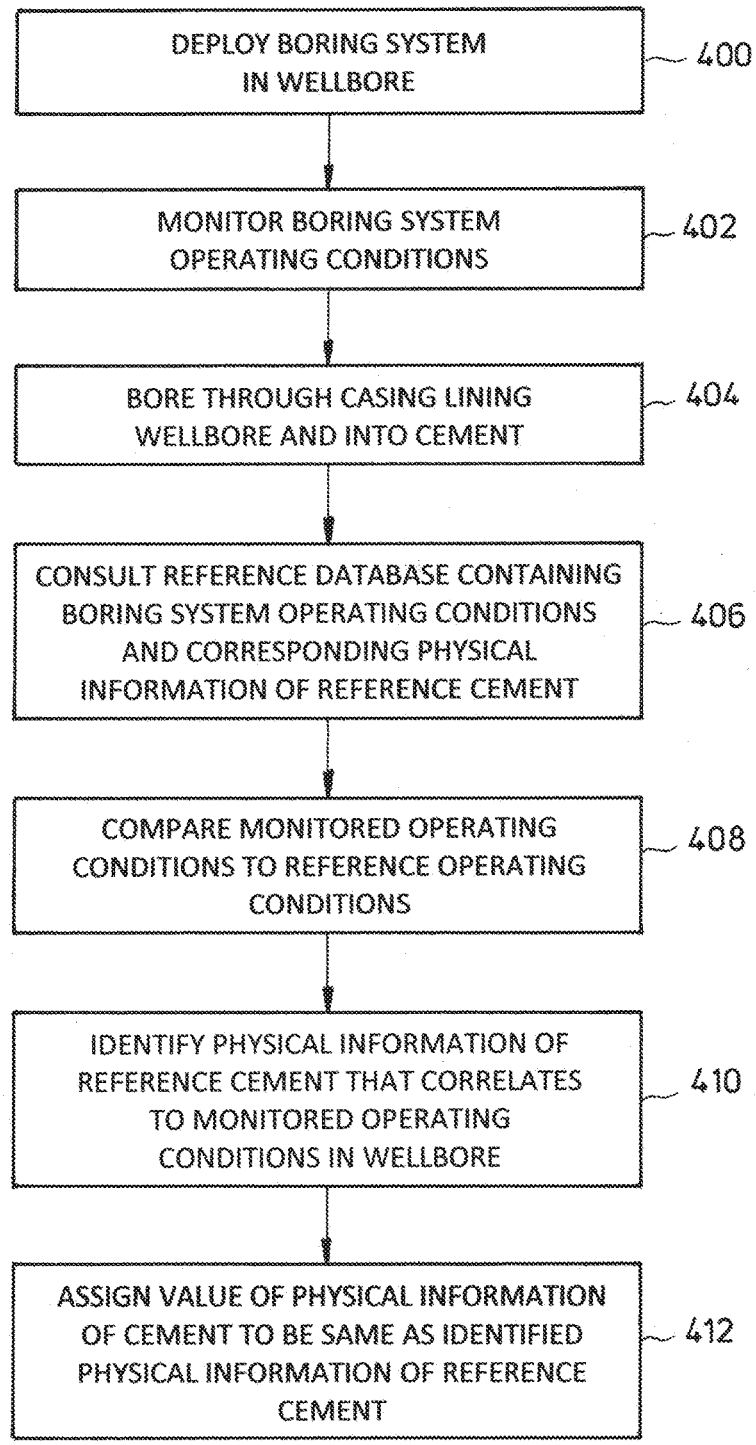
FIG. 4 includes a flowchart of an example method of obtaining physical information of cement from within a wellbore.

Provided in FIG. 4 is a flowchart depicting example steps of obtaining physical information of cement from within a wellbore. In step 400 a boring system is deployed in a wellbore, where the system includes an element for boring into cement in the wellbore, and a motor for rotating the boring element. Boring system operation conditions, such as the electricity usage, is monitored in step 402, and in step 404 the boring system is used to bore through casing lining the wellbore and into the cement. Examples exist where step 402 occurs before, during, and after step 404. In step 406 a reference database of boring system operation conditions and corresponding physical information of a reference cement is consulted. In step 408, the operating conditions monitored in step 402 are compared to the reference operating conditions consulted in step 406. Physical information of reference cement is identified in step 410, that correlates to monitored operating conditions. In step 412, value(s) of the physical information identified in step 410 is assigned to be the physical information of the cement of step 404.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. For example, multiple strings of casing can coaxially circumscribe the wellbore 12, and where cement is disposed between each string of casing. In this example, the bit 32 can drill through the multiple layers of casing and cement. In another embodiment, the bit 32 cuts through the multiple layers of casing and cement and also into the formation. As such core samples 38 can be obtained having a sample of formation along with multiple pieces of casing and cement. These and other similar modifications will readily suggest themselves to those skilled in the art, and are intended to be encompassed within the spirit of the present invention disclosed herein and the scope of the appended claims.

What is claimed is:

1. A method of operations in a wellbore comprising:
deploying a testing assembly in the wellbore, the testing assembly comprising a motor and a bit;
rotating the bit by energizing the motor;
monitoring operational data of the motor;

boring the bit into cement that lines the wellbore;

consulting a reference database that comprises physical information of a plurality of reference cements, and reference operational data of a reference motor when boring into each of the plurality of reference cements; and establishing physical information of the cement that lines the wellbore by correlating the monitored operational data with the physical information of the reference cement.

2. The method of claim 1, wherein the operational data comprises electricity delivered to the motor, and wherein the reference operational data comprises electricity delivered to the reference motor.

3. The method of claim 1, further comprising analyzing the results of acoustic testing of the cement to obtain additional information about the physical information of the cement.

4. The method of claim 1, further comprising refining results inferred from an acoustic interrogation of the wellbore with the physical information of the cement established by correlating the monitored operational data with the physical information of the reference cement.

5. The method of claim 1, wherein the bit comprises a coring bit, and wherein a core sample of the cement is retrieved and analyzed.

6. The method of claim 5, further comprising recording a force required to break the core sample from the cement.

7. The method of claim 1, wherein the bit comprises a drill bit having a helical flute.

8. The method of claim 1, wherein the physical information comprises a physical property of the cement that is selected from the group consisting of mechanical specific energy, unconfined compressive strength, yield strength, density, and combinations thereof.

9. The method of claim 1, further comprising assessing a need to remediate the cement based on the step of establishing physical information of the cement.

10. The method of claim 1, wherein the step of monitoring operational data of the motor is conducted prior to contacting the casing with the bit, while the bit is boring in the casing and cement, and after the bit is removed from the casing and the cement.

11. The method of claim 1, further comprising confirming cement presence and integrity when forming holes prior to a cement squeeze operation.

12. The method of claim 1, further comprising confirming that the cement provides a barrier to isolate subterranean zones from one another.

13. The method of claim 1, further comprising generating the reference database by using the reference motor to bore into a plurality of reference sample assemblies, that each comprise reference casing and the reference cement, and by monitoring the electricity delivered to the reference motor when boring into each reference sample assembly, and populating the reference database with values of the monitored electricity that correspond to the reference cement being bored.

14. A method of operations in a wellbore comprising:

boring into a sidewall of the wellbore with a testing assembly;

monitoring operational data of the testing assembly when the testing assembly is boring into the sidewall;

consulting a reference database that comprises physical information of a reference sidewall and reference operational data of a reference motor when boring into the reference sidewall;

identifying reference operational data from the reference database having a value substantially the same as the monitored operational data; and estimating physical information of the cement in the wellbore to be the same as reference physical information that corresponds to the identified reference operational data.

15. The method of claim 14, wherein the testing assembly comprises a motor and a bit, and wherein the bit bores into the sidewall, and wherein the sidewall comprises casing, cement, and subterranean formation.

16. The method of claim 14, wherein the operational data comprises electricity delivered to the motor, and wherein the physical information comprises unconfined compressive strength.

17. A method of operations in a wellbore comprising:

penetrating a sidewall of the wellbore;

monitoring an amount of energy consumed to penetrate the sidewall;

comparing the amount of energy consumed to an amount of energy consumed when penetrating a sidewall having known physical information; and estimating physical information about the cement based on the step of comparing.

18. The method of claim 17, wherein the physical information comprises mechanical specific energy, unconfined compressive strength, the Poisson ratio, Young's modulus, yield strength, density, and other mechanical properties.

19. The method of claim 17, wherein the sidewall comprises casing, cement, and formation, the method further comprising penetrating a plurality of samples of cement having known physical information, and monitoring amounts of energy consumed to penetrate each sample, and creating a database that correlates the amount of energy consumed for penetrating the cement.

* * * * *